(12) United States Patent
De Reuse et al.

(10) Patent No.: US 7,517,666 B2
(45) Date of Patent: *Apr. 14, 2009

(54) **METHODS OF INHIBITING *HELICOBACTER PYLORI***

(75) Inventors: Hilde De Reuse, Paris (FR); Stéphane Skouloubris, Paris (FR); Valérie Cussac, Paris (FR); Agnés Labigne, Bures-sur-Yvette (FR)

(73) Assignee: Institut Pasteur, Paris (FR)

( * ) Notice: Subject to any disclaimer, the term of this patent is extended or adjusted under 35 U.S.C. 154(b) by 247 days.

This patent is subject to a terminal disclaimer.

(21) Appl. No.: 11/068,826

(22) Filed: Mar. 2, 2005

(65) Prior Publication Data

US 2005/0176077 A1    Aug. 11, 2005

Related U.S. Application Data

(60) Continuation of application No. 10/720,470, filed on Nov. 25, 2003, now abandoned, which is a division of application No. 09/742,361, filed on Dec. 22, 2000, now Pat. No. 6,762,051, which is a continuation of application No. PCT/EP99/04490, filed on Jun. 29, 1999, which is a continuation-in-part of application No. 09/107,383, filed on Jun. 30, 1998, now Pat. No. 6,190,667.

(51) Int. Cl.
*C12Q 1/18*    (2006.01)
*C12Q 1/58*    (2006.01)
*C07K 16/12*   (2006.01)

(52) U.S. Cl. .................. 435/32; 424/234.1; 424/780; 435/69.1; 435/252.2

(58) Field of Classification Search ............... None
See application file for complete search history.

(56) References Cited

U.S. PATENT DOCUMENTS

| H25 H | 2/1986 | Radel .......................... 71/6 |
|---|---|---|
| 5,190,961 A | 3/1993 | Hasegawa et al. ............ 514/331 |
| 5,214,053 A | 5/1993 | Nakazawa et al. ........... 514/318 |
| 5,409,903 A | 4/1995 | Polak et al. .................... 514/23 |
| 5,441,875 A | 8/1995 | Hediger ...................... 435/69.1 |

(Continued)

FOREIGN PATENT DOCUMENTS

EP    0 367 644    5/1990

(Continued)

OTHER PUBLICATIONS

Sjostrom, JE et al, Antimicrobial Agents and Chemotherapy, Mar. 1996, pp. 621-626, vol. 40(3), In vitro antibacterial activity of omeprazole and its selectivity for *Helicobacter* spp. are dependent on Incubation Conditions.*

(Continued)

*Primary Examiner*—Mark Navarro
*Assistant Examiner*—Ginny Portner
(74) *Attorney, Agent, or Firm*—Finnegan, Henderson, Farabow, Garrett & Dunner L.L.P.

(57) ABSTRACT

This application relates to methods of screening molecules capable of inhibiting the survival of *Helicobacter pylori* in vivo by specifically inhibiting the activity of UreI, to the molecules identified by these methods, and to the use of these molecules to treat or prevent *H. pylori* infection.

9 Claims, 9 Drawing Sheets

U.S. PATENT DOCUMENTS

| | | | |
|---|---|---|---|
| 5,514,660 | | 424/195.1 A | 5/1996 |
| 5,4%2,695 | | 12/1995 | Neeman et al. |
| 5,514,660 A | 5/1996 | Zopf et al. | 514/25 |
| 5,560,912 A | 10/1996 | Neeman et al. | 424/195.1 |
| 5,695,931 A | 12/1997 | Labigne | 435/6 |
| 5,843,460 A | 12/1998 | Labigne et al. | 424/234.1 |
| 5,876,946 A | 3/1999 | Burbaum et al. | 435/7.1 |
| 5,900,410 A | 5/1999 | Hartmann | 514/81 |
| 5,942,409 A * | 8/1999 | Sachs et al. | 435/32 |
| 5,985,631 A | 11/1999 | Soman et al. | 435/184 |
| 5,986,051 A * | 11/1999 | Labigne et al. | 530/350 |
| 6,027,878 A * | 2/2000 | Labigne et al. | 435/6 |
| 6,087,358 A | 7/2000 | Baker et al. | 514/230.5 |
| 6,124,271 A | 9/2000 | Iversen et al. | 514/44 |
| 6,149,908 A | 11/2000 | Claesson et al. | 424/94.4 |
| 6,190,667 B1 * | 2/2001 | De Reuse et al. | 424/234.1 |
| 6,258,359 B1 * | 7/2001 | Labigne et al. | 424/141.1 |
| 6,271,017 B1 * | 8/2001 | Labigne et al. | 435/252.3 |
| 6,416,968 B1 * | 7/2002 | De Reuse et al. | 435/32 |
| 6,476,213 B1 | 11/2002 | Suerbaum et al. | 536/23.7 |
| 6,762,051 B2 * | 7/2004 | De Reuse et al. | 435/320.1 |
| 2004/0142343 A1 * | 7/2004 | Chang et al. | 435/6 |

FOREIGN PATENT DOCUMENTS

| | | |
|---|---|---|
| EP | 0 745 674 | 12/1996 |
| WO | WO 91/09049 | 6/1991 |
| WO | WO 93/07273 | 4/1993 |
| WO | WO 94/09823 | 5/1994 |
| WO | WO 94/26901 | 11/1994 |
| WO | WO 96/33732 | 10/1996 |
| WO | WO 96/40893 | 12/1996 |
| WO | WO 97/26908 | 7/1997 |
| WO | WO 98/17804 | 1/1998 |

OTHER PUBLICATIONS

Ferrero, RL et al, 1994, In Basic and Clinical Aspects of H.pylori infection, Springer, Verlag, Berlin Heidelberg, pp. 179-182, Construction of isogenic mutants of *Helicobacter pylori* deficient in urease activity.*

Scott, David et al, Trends in Microbiology, vol. 8(8), Aug. 2000, pp. 348-349, UreI-mediated urea transport in *Helicobacter pylori*: an open and shut case? Response.*

Ito, Ytaka e tal, European Jorunal of Pharmacology, vol. 345, pp. 193-198, 1998, Ecabet sodium, a locally acting antiulcer drug, inhibits urease activity of *Helicobacter pylori*.*

Sjostrom, JE et al, J. Med. Microbiol., Jun. 1996, vol. 44(6), pp. 425-433, Factors affecting growth and antibitotic susceptibility of *Helicobacter pylori*: effect of pH and urea on the survival of the wild-type strain and a urease-deficient mutant (abstract only).*

Skouloubris, S et al, Mol. Microbiology, Sep. 1997, vol. 25(5), pp. 989-998, Identification and characterization of an aliphatic amidase in *Helicobacter pylori* (abstract only).*

Akada, J. et al., "Transcriptional Analysis of Urease Structural Genea and the UreI Gene in *Helicobacter pylori*," GUT, 41:A9 (1997).

Akada, J. et al., "European *Helicobacter pylori* Study Group Xth International Workshop on Gastroduodenal Pathology and *Helicobacter pylori*," GUT, 41(1):A7-A8 (1997).

Chebrou, H. et al., "Amide Metabolism: a putative ABC transporter in *Rhodococcus* sp. R312," Gene, 182:215-218 (1996).

Clyne et al., "*Helicobacter pylori* Reqires an Acidic Environment to Survive in the Presence of Urea," Infection and Immunity, 63(5):1669-1673 (1995).

Coudron, P. E. et al., "Factors Affecting Growth and Susceptibility Testing of *Helicobacter pylori* in Liquid Media," Journal of Clinical Microbiology, 33(4):1028-1030 (1995).

Coudron, P. E. et al., "Use of Time-Kill Methodology To Assess Antimicrobial Combinations against Metronidazole-Susceptible and Metronidazole-Resistant Strains of *Helicobacter pylori*," Antimicrobial Agents and Chemotherapy, 39(12):2641-2644 (1995).

Coudron, P. E. et al., "Utilization of Time-Kill Kinetic Methodologies for Assessing the Bactericidal Activities of Ampicillin and Bismuth, Alone and in Combination, against *Helicobacter pylori* in Stationary and Logarithmic Growth Phases," Antimicrobial Agents and Chemotherapy, 39(1):66-69, (1995).

Cussac, V. et al., "Expression of *Helicobacter pylori* Urease Activity in *Escherichia coli* Host Strains," Society for Microbial Ecology and Disease, 4(S):S139, Abstract H4-4 (1991).

Cussac, V. et al., "Expression of *Helicobacter pylori* Urease Genes in *Escherichia coli* Grown under Nitrogen-Limiting Conditions," Journal of Bacteriology 174(8):2466-2473 (1992).

DeCross, A. J. et al., "Metronidazole Susceptibility Testing for *Helicobacter pylori*: Comparison of Disk, Broth, and Agar Dilution Methods and Their Clinical Relevance," Journal of Clinical Microbiology, 31(8):1971-1974 (1993).

Eaton, K. A. et al., "Essential Role of Urease in Pathogenesis of Gastritis Induced by *Helicobacter pylori* in Gnotobiotic Piglets," Infection and Immunity, 59(7):2470-2475 (1991).

Ferrero, R. et al., "Construction of Urease Deficient Mutants of *Helicobacter pylori* By Allelic Exchange," Society for Microbial Ecology and Disease, 4(S):S136, Abstract H4-1 (1991).

Ferrero, R. L. et al., "The Importance of Urease in Acid Protection for the Gastric-colonising Bacteria *Helicobacter pylori* and *Helicobacter felis* sp. nov.," Microbial Ecology in Health and Disease, 4:121-134 (1991).

Garcia-Rodriguez, J. A. et al., "In Vitro Activity of Six Antacids and a Urease Inhibitor Against *Helicobacter pylori*," Revista Espanola de Quimioterapia, Spain, 4(4):336-337 (1991).

Gregoriou, M. et al., "Inhibition of the Aliphatic Amidase from *Pseudomonas aeruginosa* by Urea and Related Compounds," Eur. J. Biochem., 96:101-108 (1979).

Hollaway, M. R. et al., "Chloroacetone as an Active-Site-Directed Inhibitor of the Aliphatic Amidase from *Pseudomonas aeruginosa*," Biochem. J, 191:811-826 (1980).

Ito, Y. et al., "Ecabet sodium, a locally acting antiulcer drug, inhibits urease activity of *Helicobacter pylori*," European Journal of Pharmacology, 345:193-198 (1998).

Kühler, T. C. et al., "Structure—Activity Relationship of Omeprazole and Analogues as *Helicobacter pylori* Urease Inhibitors," J. Med. Chem., 38:4906-4916 (1995).

Labigne, A. et al., "Shuttle Cloning and Nucleotide Sequences of *Helicobacter pylori* Genes Responsible for Urease Activity," Journal of Bacteriology, 173(6):1920-1931 (1991).

Labigne, A. et al., Bull. Acad. Natle, Med., "Development of genetic and molecular approaches for the diagnosis and study of the pathogenesis of *Helicobacter pylori* induced gastroduodenal diseases," 175(6):791-802 (1991).

Malanoski, G. J. et al., "Effect of pH Variation on the Susceptibility of *Helicobacter pylori* to Three Macrolide Antimicrobial Agents and Temafloxacin," European Journal of Clinical Microbiology and Infectious Diseases, 12:131-133 (1993).

McGowan, C. C. et al., "The Proton Pump Inhibitor Omeprazole Inhibits Acid Survival of *Helicobacter pylori* by a Urease-Independent Mechanism," Gastroenterology, 107: 738-743 (1994).

Midolo, P.D. et al., "Metronidazole resistance: A predictor of failure of *Helicobacter pylori* eradication by triple therapy," Journal of Gastroenterology and Hepatology, 11:290-292 (1996).

Mirshahi, F. et al., "Omeprazole may exert both a bacteriostatic and a bacteriocidal effect on the growth of *Helicobacter pylori* (NCTC 11637) in vitro by inhibiting bacterial urease activity," Journal of Clinical Pathology, 51:220-224 (1998).

Nagata, K. et al., "Inhibitory Action of Lansoprazole and Its Analogs against *Helicobacter pylori*: Inhibition of Growth Is Not Related to Inhibition of Urease," Antimicrobial Agents and Chemotherapy, 39(2):567-570 (1995).

Nawaz, M.S. et al., Appl. Environ. Microbiol., 60(9), 3343-3348 (abstract only) (Sep. 1994).

Neyrolles, O. et al., Journal of Bacteriology, 178(3):647-655 (1996).

Park, J. et al., "Kinetic Studies of *Helicobacter pylori* Urease Inhibition by a Novel Proton Pump Inhibitor, Rabeprazole," Biol. Pharm. Bull., 19(2):182-187(1996).

Pope, A. J. et al., "Effect of Potent Urease Inhibitor, Fluorofamide, on *Helicobacter* sp. in Vivo and in Vitro," Digestive Diseases and Sciences, 43(1):109-119 (1998).

Rektorschek, M. et al., Mol. Microbiology, 36(1), 141-152 (2000).

Rosenstein, I.J., *Crit. Rev. Clin. Lab. Sci.*, 23(3), 245-277 (1986).

Scott, et al., "The Role of Internal Urease in Acid Resistance of *Helicobacter pylori*," *Gastroenterology* 114:58-70 (1998).

Sjostrom, J. E. et al., "Factors Affecting Growth and Antibiotic Susceptibility of *Helicobacter pylori*: effect of pH and urea on the survival of a wild-type strain and a urease-deficient mutant," *J. Med. Microbiology*, 44, 425-433 (1996).

Skouloubris, S.A. et al., *Mol. Microbiology*, 25, 989-998 (1997).

Skouloubris, et al., "The *Helicobacter pylori* UreI Protein is not Involved in Urease Activity but is Essential for Bacterial Survival in vivo," *Infection and Immunity*, 66(9):4517-4521 (1998).

Sugiyama, T. et al., "A Novel Enzyme Immunoassay for Serodiagnosis of *Helicobacter pylori* Infection," *Gastroenterology*, 101:77-83 (1991).

Wilson, S. A. et al., "Identification of Two New Genes in the *Pseudomonas aeruginosa* Amidase Operon, Encoding an ATPase (AmiB) and a Putative Integral Membrane Protein (AmiS)," *The Journal of Biological Chemistry*, 270(32), 18818-18824 (1995).

Woods, M. J. et al., "Selective Inhibition and the Kinetic Mechanism of the Aliphatic Amidase of *Pseudomonas aeruginosa*," *Biochemical Society Transactions*, 2:1344-1346 (1974).

* cited by examiner

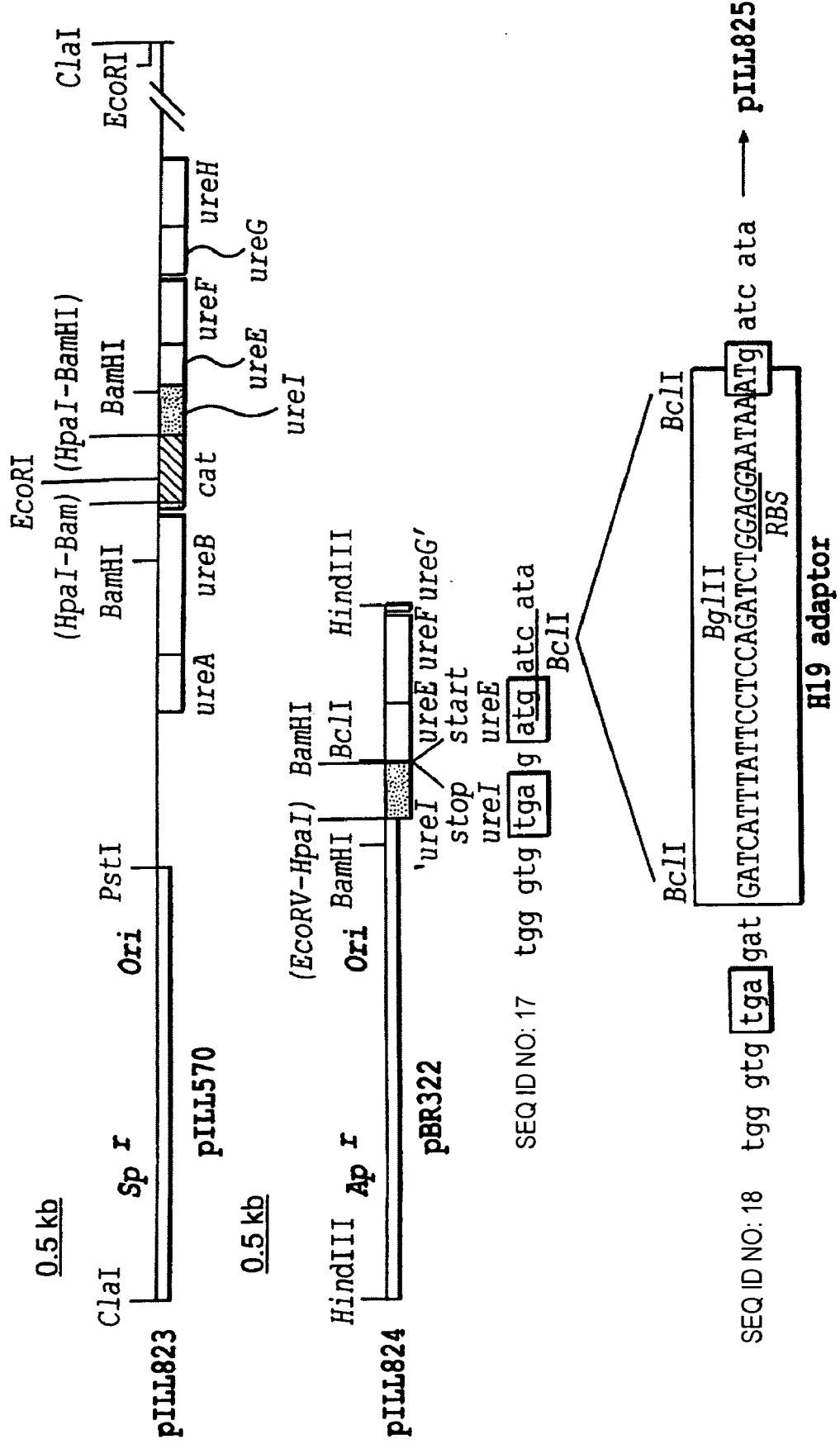
FIG. 2A1

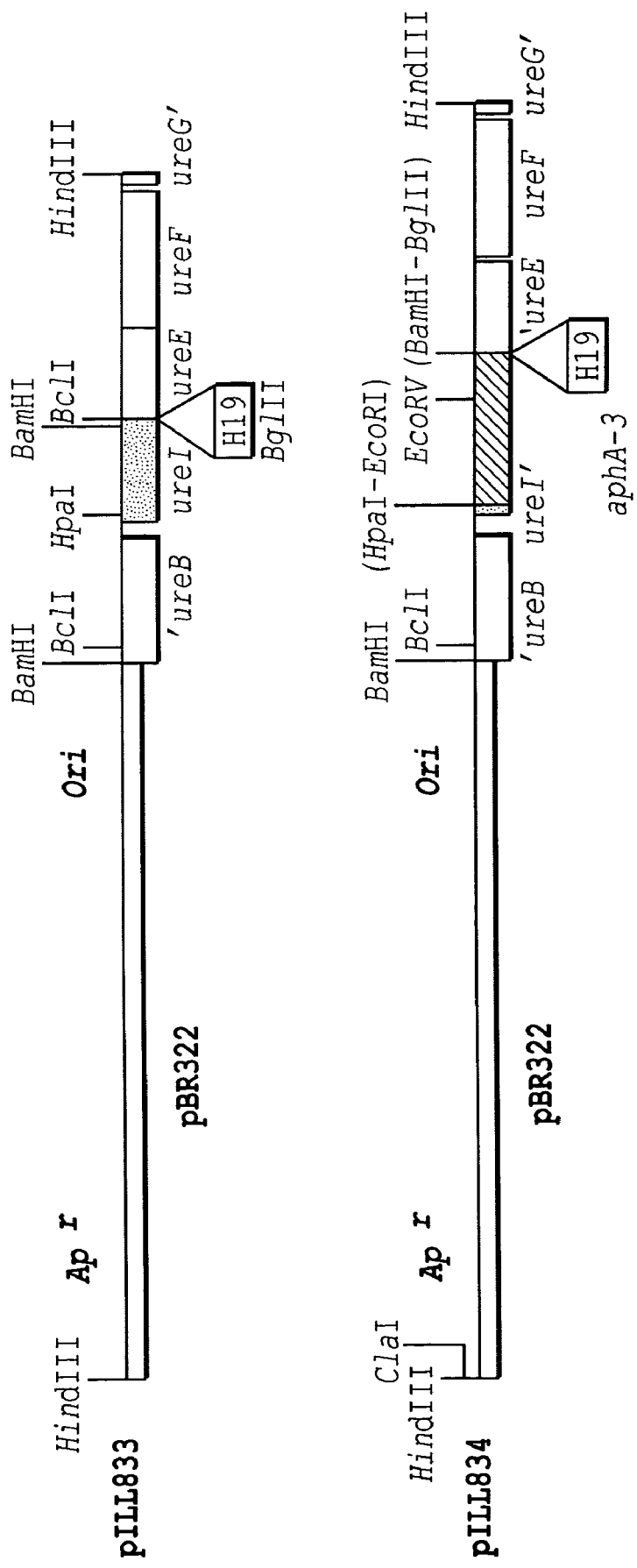
*FIG. 2A2*

FIG. 3A

FIG. 3B pH 7
Panel A:
strain N6
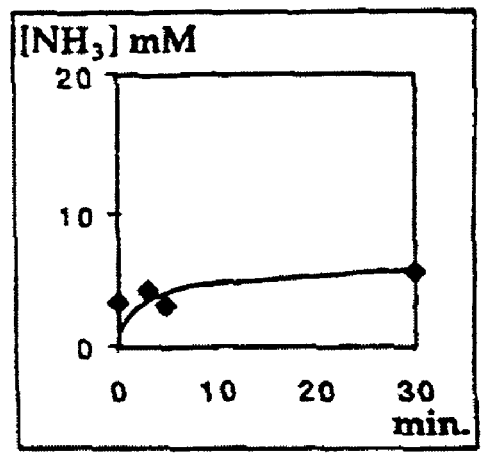
FIG. 4A1
Panel B:
N6-834
($\Delta ureI$)
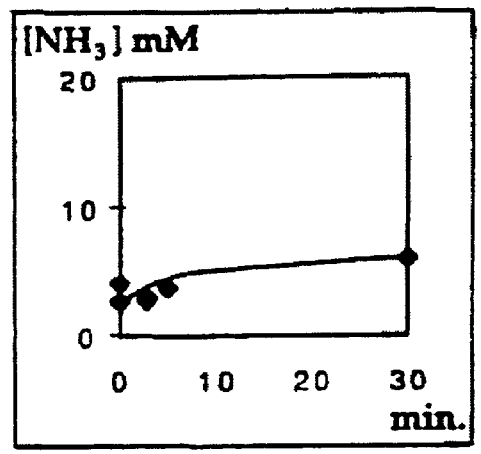
FIG. 4A2 pH 5
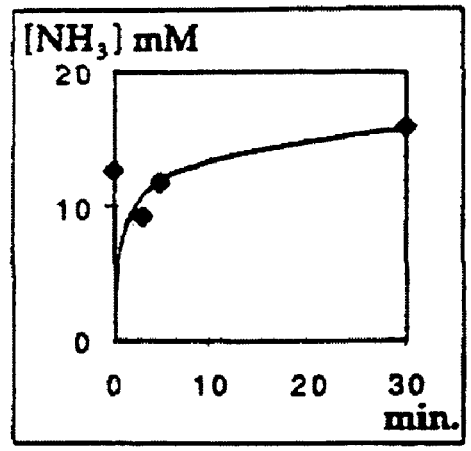
Panel A :
strain N6
FIG. 4B1
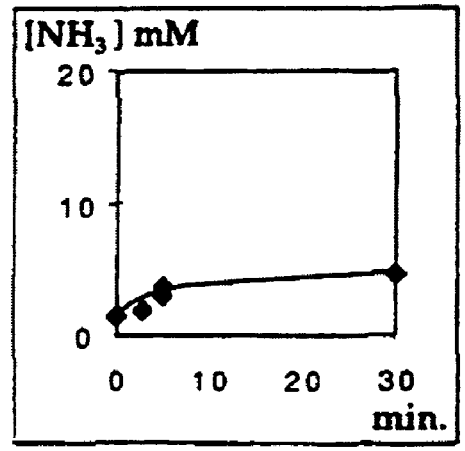
Panel B :
N6-834
(Δure1)
FIG. 4B2 pH 2.2
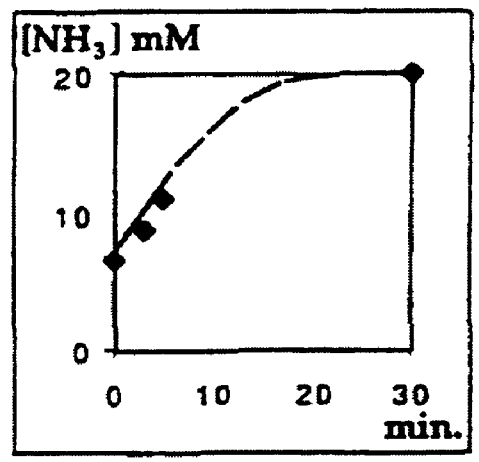
Panel A: strain N6
FIG. 4C1
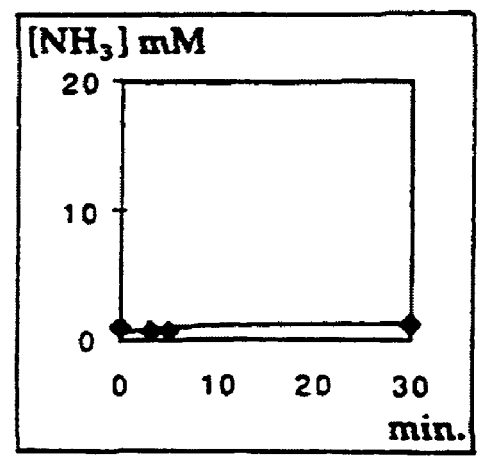
Panel B: N6-834 (ΔureI)
FIG. 4C2

METHODS OF INHIBITING *HELICOBACTER PYLORI*

This is a continuation of application Ser. No. 10/720,470, filed Nov. 25, 2003 now abandoned, which is a division of application Ser. No. 09/742,361, filed Dec. 22, 2000, which issued as U.S. Pat. No. 6,762,051 on Jul. 13, 2004, which is a continuation of International Application No. PCT/EP99/04490, filed Jun. 29, 1999, which in turn is a continuation-in-part of U.S. application Ser. No. 09/107,383, filed Jun. 30, 1998, which issued as U.S. Pat. No. 6,190,667 on Feb. 20, 2001. The entire disclosure of these applications is relied upon and incorporated by reference herein.

This invention relates to methods of screening molecules capable of inhibiting the survival of *Helicobacter*, particularly *Helicobacter pylori*, in vivo by specifically inhibiting the activity of UreI, to the molecules identified by these methods, and to the use of these molecules to treat or prevent *Helicobacter* infection.

BACKGROUND OF INVENTION

*Helicobacter pylori* is a microaerophilic Gram-negative bacterium, which colonizes the gastric mucosa of humans (10). *H. pylori* is associated with gastritis and peptic ulcer disease and has been shown to increase the risk of gastric cancers. Urease is a major virulence factor of *H. pylori*. It is involved in neutralizing the acidic microenvironment of the bacterium and also plays a role in *H. pylori* metabolism (11, 26).

The urease region of the *H. pylori* genome is composed of two gene clusters common to all strains (9 and FIG. 1), one comprising the ureAB genes encoding the structural urease subunits and the other containing the ureEFGH genes encoding the accessory proteins required for nickel incorporation into the urease active site. The ureI gene lies immediately upstream from this latter gene cluster and is transcribed in the same direction (FIG. 1). The ureA, ureB, ureE, ureF, ureG, ureH, and ureI genes and gene products have been described and claimed in U.S. Pat. No. 5,695,931 and allowed patent application Ser. No. 08/472,285, both of which are specifically incorporated herein by reference.

The distances separating ureI from ureE (one base pair, bp) and ureE from ureF (11 bp) suggest that ureI-ureE-ureF constitute an operon. Cotranscription of ureI and ureE has been demonstrated by northern blot analysis (1). An *H. pylori* N6 mutant with a ureI gene disrupted by a MiniTn3-Km transposon was previously described by Ferrero et al. (1994) (13). This strain (N6-ureI::TnKm-8) presented a urease negative phenotype, so it was concluded that ureI was an accessory gene required for full urease activity.

The sequences of UreI from *H. pylori* and the AmiS proteins, encoded by the aliphatic amidase operons of *Pseudomonas aeruginosa* and *Rhodococcus* sp. R312, are similar (5, 27). Aliphatic amidases catalyze the intracellular hydrolysis of short-chain aliphatic amides to produce the corresponding organic acid and ammonia. It has been shown that *H. pylori* also has such an aliphatic amidase, which hydrolyzes acetamide and propionamide in vitro (23).

In view of the sequence similarity between UreI and AmiS together with the very similar structures of the urease and amidase substrates (urea: $NH_2$—CO—$NH_2$ and acetamide: $CH_3$—CO—$NH_2$) and the production of ammonia by both enzymes, a better understanding of the function of the *H. pylori* UreI protein is required. This understanding will open new opportunities for the prevention and treatment of *H. pylori* infections.

SUMMARY OF THE INVENTION

This invention provides methods for identifying molecules capable of inhibiting the growth and/or survival of *Helicobacter* species, particularly, *H. pylori*, in vivo. In particular, the methods of this invention involve screening molecules that specifically inhibit UreI protein function.

The invention encompasses the molecules identified by the methods of this invention and the use of the molecules by the methods of this invention to treat or prevent *Helicobacter*, and particularly *H. pylori*, infection in humans and animals.

Another aspect of this invention is a method of preventing or treating *Helicobacter* species infection by administration to a human or animal in need of such treatment a molecule capable of inhibiting the growth and/or survival of *Helicobacter* species in vivo. One such molecule according to the invention is characterized by a high affinity for UreI, which allows it (i) to be transported inside the *Helicobacter* cell, or (ii) to inhibit transport properties of UreI, or (iii) to inhibit UreI function by inhibiting UreI interaction with urease or other *Helicobacter* proteins. By inhibiting UreI, such molecule renders the bacteria more sensitive to acidity.

Yet another aspect of this invention is the production of immunogenic UreI antigens and their use as vaccines to prevent *Helicobacter* species infection and/or colonization of the stomach or the gut. Antibodies to these UreI antigens are also encompassed within the scope of this invention.

This invention further relates to recombinant strains of *H. pylori* comprising a modified ureI gene, such that the products of the modified gene contribute to the attenuation of the bacteria's ability, to survive in vivo, and thus, its pathogenic effects.

BRIEF DESCRIPTION OF THE FIGURES

FIG. 2A is divided into two sheets, FIG. 2A1, which depicts restriction maps of pILL823 and pILL824, and FIG. 2A2, which depicts restriction maps of pILL833 and pILL834. In each restriction map of FIGS. 2A1 and 2A2, small boxes mark the vector of each plasmid, and large boxes correspond to genes. Ori indicates the position of the ColE1 origin of replication. $Sp^R$ and $AP^R$ are the genes conferring resistance to spectinomycin and ampicillin, respectively. Cassettes inserted into ureI and conferring resistance to chloramphenicol (cat) or kanamycin (aphA-3) are also shown. The sequence of the DNA region (SEQ ID NO: 17) comprising the ureI stop codon and the ureE start codon, including the BclI site where adaptor H19 (SEQ ID NO: 18) was inserted, is given. Insertion of H19 into the BclI site of pILL824 produced pILL825, the resulting ureI-ureE intergenic region is also shown (FIG. 2A1). The stop codon of ureI and the start codon of ureE are boxed and the ribosome binding site (RBS) is underlined. Brackets indicate the position of restriction sites removed by ligation.

FIGS. 3A and 3B show the alignment of the amino acid sequence of UreI from *H. pylori* with those of similar proteins and prediction of the two-dimensional structure of members of the UreI/AmiS protein family. FIG. 3B is a continuation of FIG. 3A. Residues that are identical at one position in at least four sequences are boxed. Dashes indicate gaps that have been inserted to optimize alignment. The organisms from which the sequences originated and the degree of identity with the *H. pylori* UreI protein are: UreI-Hp, *Helicocobacter pylori* (195 residues, Accession No. M84338) (SEQ ID NO: 10); UreI-Hf, *Helicobacter felis* (74% identity over 196 residues, Accession No. A41012) (SEQ ID NO: 11); UreI-Lacto, *Lactobacillus fermentum* (55% identity over the 46 residues-long partial sequence, Accession No. D10605) (SEQ ID NO: 12); UreI-Strepto, *Streptococcus salivarius* (54% identity over the 129 residues-long partial sequence, Accession No. U35248) (SEQ ID NO: 13); AmiS-Myco, *Mycobactenium smegmatis* (39% identity over 172 residues, Accession No. X57175) (SEQ ID NO: 14); AmiS-Rhod, *Rhodococcus sp.* R312 (37% identity over 172 residues, Accession No. Z46523) (SEQ ID NO: 15), and AmiS-Pseudo, *Pseudomonas aeruginosa* (37% identity over 171 residues, Accession No. X77161) (SEQ ID NO: 16). Predicted transmembrane α-helices are shown as shaded boxes. The regions separating these boxes are hydrophilic loops labeled "IN" when predicted to be intracellular and "OUT" when predicted to be extracellular.

FIG. 4 depicts the kinetics of ammonium release by the N6 parental strain (panel A) and the UreI-deficient strain N6-834 (panel B). Bacteria ($2 \times 10^8$/ml) were harvested and washed (as described in Skouloubris et al. (30)) resuspended in 10 ml of phosphate saline buffer (PBS) at pH 7, 5 or 2.2 in the presence of 10 mM urea. After 0, 3, 5 and 30 minutes, 0.5 ml were withdrawn and centrifuged to eliminate bacteria. The supernatant was kept on ice until ammonium concentration was measured using the assay commercialized by Sigma (kit reference #171).

Figure 1:
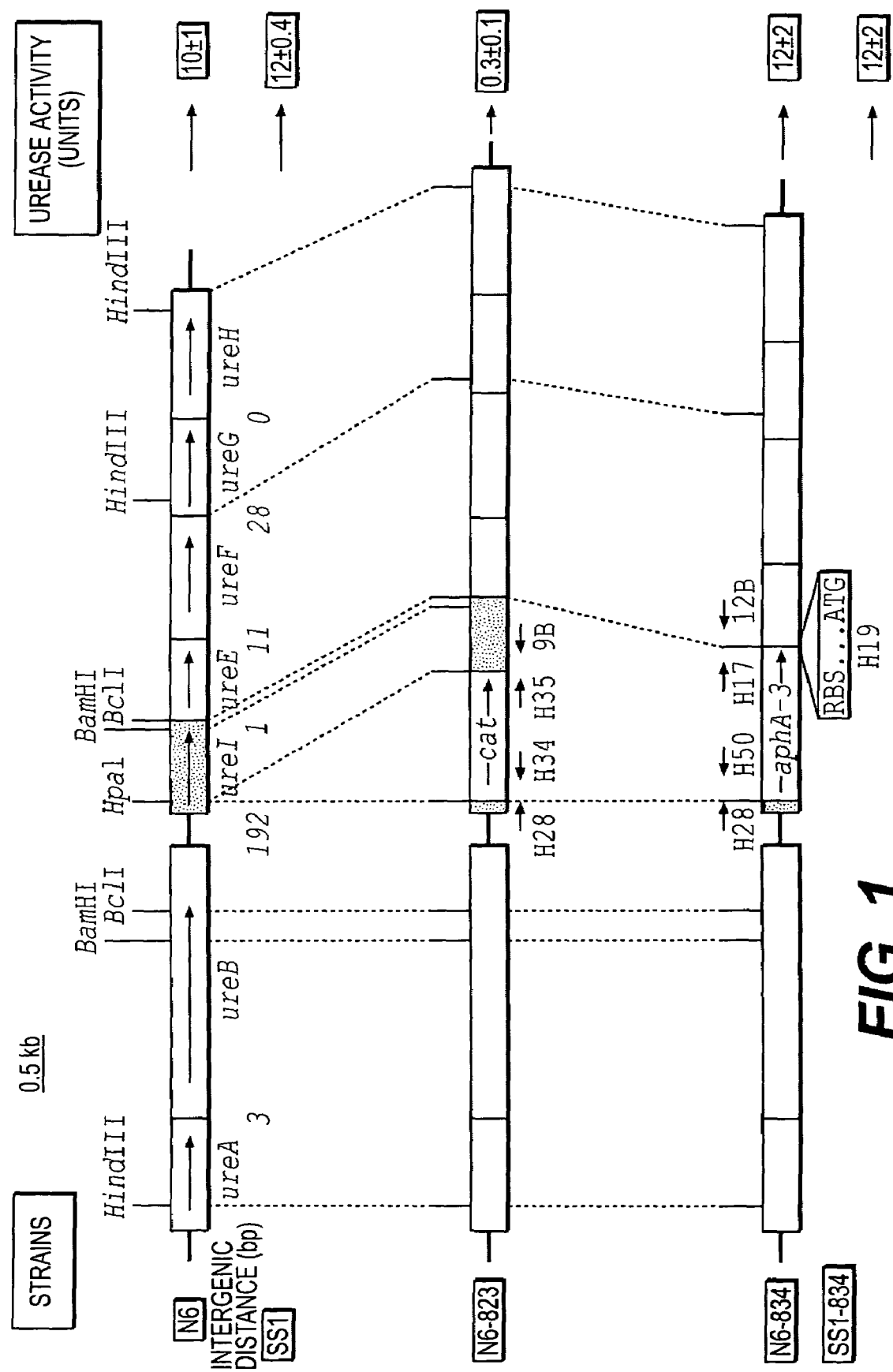
FIG. 1 depicts the urease gene cluster of *H. pylori* parental strains N6 and SS1 and of the derived mutants deficient in UreI, strains N6-823, N6-834, and SS1-834. The genes are indicated by boxes with an arrow showing the direction of their transcription. The distances between the ure genes are given in base pairs, bp. The site hybridizing to the primers used to confirm correct allelic exchange in strains N6-823, N6-834, and SS1-834 is shown. Blank boxes represent the cassettes containing the genes conferring resistance to Cm (cat) or to Km (aphA-3). The urease activity of these strains is given on the right-hand side of the figure. Urease activity was measured as the release of ammonia on crude extracts of bacteria grown 48 hours on blood agar plates as described previously (9). One unit corresponds to the amount of enzyme required to hydrolyze 1 μmol of urea $min^{-1}$ $mg^{-1}$ total protein. The data are means±standard deviation calculated from 3 to 5 determinations.

Table 2 shows the results obtained with the in vitro viability tests and the pH measurements.

Table 3 gives the values of ammonium production by strain N6 and N6-834 presented on the graphs of FIG. 4.

DETAILED DESCRIPTION

The urease cluster of *Helicobacter* species is unique among the many urease operons of Gram-negative bacteria that have been sequenced (20) in that it has an extra gene, ureI. The function of UreI has therefore been the subject of much speculation. It has mostly been attributed the function of an accessory protein required for nickel incorporation at the urease active site or a nickel transporter. A *H. pylori* strain carrying a deletion of ureI replaced by a non-polar cassette (Kanamycin resistance cassette) has been constructed and was named N6-834 (30). The strain has been deposited at C.N.C.M. (Collection Nationale de Culture de Microorganismes, 25 rue du Docteur Roux, 75724 Paris Cédex 15, France) on Jun. 28, 1999. This is the first time that a non-polar cassette (19) has been shown to be functional in *H. pylori*. These results provide a valuable tool for genetic analysis of complex *H. pylori* operons, such as Cag, a multigenic pathogenicity island.

Studies with this strain demonstrated that UreI is not required for full activity of *H. pylori* urease as measured after in vitro growth at neutral pH. This result argues against UreI being involved in nickel transport since such a protein, NixA (3) already identified in *H. pylori*, is necessary for full urease activity. Comparing ureases expressed from a UreI-deficient strain and the corresponding parental strain show that (i) they present the same activity optimum pH (pH 8); (ii) the urease structural subunits, UreA-B, are produced in equal amounts; and (iii) the urease cellular location is identical.

It is demonstrated here that (i) UreI is essential for colonization of mice by *H. pylori*; (ii) UreI is important for survival of *H. pylori* at acidic pH; and (iii) UreI is necessary for urease "activation" at low pH.

*H. pylori* during the colonization process of the stomach has to deal with important pH variations and especially has to adapt rapidly to extremely acidic pH (as acidic as pH 1.4). We have shown that UreI is required for *H. pylori* adaptation to acidity, consistently with the absence of colonization of the mouse stomach. As an essential protein for the *H. pylori* resistance to acidity, UreI certainly plays a key role in the infection, establishment, and persistence of *H. pylori*. UreI has a sequence similar to those of the AmiS proteins, proposed to be involved in the transport of short-chain amides (27), molecules structurally similar to urea. The UreI/AmiS proteins have the characteristics of integral membrane proteins, probably of the cytoplasmic membrane.

Different roles for UreI can be proposed. For instance, UreI might be involved in transport (import or export) of urea or short chain amides specifically active at low pH. However, an essential role for UreI as an amide transporter is less likely because a SS1 mutant, deficient in aliphatic amidase, colonizes as efficiently as the parental strain in mouse colonization experiments. In addition, amidase activity is not significantly modified by the deletion of ureI in the N6-834 mutant strain (C.N.C.M. filed on Jun. 28, 1999). Import or export of urea could be consistent with the existence of a urea cycle, which is one of the characteristics of *H. pylori* (28).

Alternatively, UreI might be involved in an active ammonium export system. Finally, UreI might be involved in a mechanism of coupling urease activity to the periplasmic pH, allowing urease to become more active when extracellular pH is acidic.

Our results are compatible with the first hypothesis of UreI being an urea transporter active at acidic pH values and the third hypothesis of UreI being a kind of sensor protein between the periplasmic PH and urease activity. We think that these two hypothesis are not exclusive. Whatever the role of UreI, as a membrane protein essential for the survival of *H. pylori* in vivo, it now provides a powerful target for a new eradication therapy and for vaccines against *H. pylori*.

Molecules capable of inhibiting the growth and/or survival of *Helicobacter* in vivo may be identified by contacting a parental *Helicobacter* strain with said molecule in a biological sample; testing and comparing, in the presence or absence of urea, the sensitivity to the extracellular pH of the parental strain to a strain deficient in UreI and to a UreI deficient strain complemented with ureI; selecting said molecules displaying a differential effect on the parental or complemented strain as compared to the UreI deficient strain; and collecting said, active molecule.

A molecule active specifically on UreI will be the one rendering *H. pylori* sensitive to acidic pH (pH 2.2) in the presence of urea without affecting the strain behavior at neutral pH. Sensitivity to acidity in the presence of urea can be tested on whole *H. pylori* cells following a protocol described in the examples and adapted from Clyne et al. (8). We are now trying to transpose this test in *E. coli* whole cells carrying the complete urease gene cluster on a plasmid (ureAB-ureIEFGH). Screening for a molecule rendering this recombinant *E. coli* more sensitive to acidity in the presence of urea will be performed as described for *H. pylori* in the examples. To distinguish between inhibitory molecules acting on UreI and those acting on urease, the medium pH after whole cell incubation at pH 7 in the presence of urea will be measured. Interesting molecules are those affecting response to acidity without inhibiting the alkalization of the medium observed after incubation at neutral pH.

These methods may be used to identify molecules that inhibit any *Helicobacter* species carrying a UreI-homolog. This includes the gastric *Helicobacter* species: *Helicobacter pylori*, *Helicobacter felis*, *Helicobacter mustelae*, *Helicobacter muridarum*, and also *Helicobacter heiimannii*, *Helicobacter canis*, *Helicobacter bilis*, *Helicobacter hepaticus*, and *Helicobacter troguntum*.

The molecules identified by the methods of this invention will be capable of inhibiting UreI activity by (i) inhibiting transport of urea or short chain amides, (ii) inhibiting ammonium export, or (iii) inhibiting urease "activation" at low pH. The molecules according to point (i) and (ii) should be able to diffuse throughout the outer membrane and should be active even at low concentration. Suitable candidate molecules are structural analogs of urea or short chain amides, ammonium derivatives or urease inhibitors. For example, molecules derived from AHA (acetohydroxamic acid), hydroxyurea, hippuric acid, flurofamide, hydroxylamine, methylurea, thiourea (29), or methylammonium. The molecules according to point (iii) should inhibit the contact between UreI (probably inserted in the cytoplasmic membrane) and periplasmic, membrane, or cytoplasmic *H. pylori* proteins, which are necessary for urease "activation" at low pH. These proteins could be the structural subunits of urease itself, the accessory proteins, or other proteins. Molecules obtained according to this invention should not be urease competitive inhibitors, should not be toxic or mutagenic in vivo and could potentialize the action of antibiotics or bactericidal molecules. Validation of the action of such molecules could be performed in vivo in the mouse animal model with the pair of isogenic strains SS1 ad SS1-834 as described in the examples.

One example of a molecule according to this invention is a monoclonal or polyclonal antibody specific for UreI. Preferably, the antibody is capable of specifically inhibiting UreI activity.

The molecules of this invention may be administered in combination with a pharmaceutically acceptable carrier to a patient suffering from a *Helicobacter* infection. Alternatively, immunogenic compositions comprising one or more molecules according to this invention may be administered in a vaccine composition to prevent infection by *Helicobacter* species.

Immunogenic compositions according to this invention may also comprise all or part of the UreI protein. Preferably, the UreI fragments comprise at least 10 consecutive amino acids of the native UreI sequence and more preferably, the fragments comprise at least 18, 20, or 25 consecutive amino acids of the native UreI sequence. Other suitable UreI fragments may contain at least 40 or at least 100 consecutive amino acids of the native UreI sequence. Suitable fragments of *Helicobacter pylori* include, for example, fragments selected from the croup consisting of amino acid residues 22 to 31, 49 to 74, 94 to 104, and 123 to 142 of *H. pylori* (GenBank accession No. M84338)

Reference will now be made to the following Examples. The Examples are purely exemplary of the invention and are not to be construed as limiting of the invention.

EXAMPLES

Construction of Defined Mutations of the *H. pylori* ureI Gene

*H. pylori* strains with defined mutations in ureI were generated by allelic exchange to determine whether the UreI protein was necessary for production of active urease. For this purpose, two plasmids (pILL823 and pILL834) with cassettes carrying antibiotic resistance genes inserted in ureI were constructed in *E. coli*.

In one plasmid, pILLS823 (FIG. 2A), the ureI gene was inactivated by insertion of a promoterless cat gene, conferring resistance to chloramphenicol (Cm). A 780 bp blunt-ended BamHI restriction fragment containing the "cat cartridge" from pCM4 (Pharmacia, Sweden) was introduced into a unique HpaI site, between codons 21 and 22 of ureI, in pILL753 (9). In the resulting plasmid, pILL823 (FIG. 2A), cat is in the same orientation as ureI and is expressed under the control of the ureI promoter.

The second plasmid, pILL834, carried a ureI gene in which all but the first 21 codons were deleted and replaced with a non-polar cassette composed of the aphA-3 kanamycin (Km) resistance gene (25), which has been deleted from its own promoter and terminator regions (19). In *Shigella flexneri* (19) and other organisms (such as *Yersinia enterocolitica*, 2) this cassette has been shown not to affect the transcription of the genes downstream within an operon as long as these distal genes have intact translation signals. There is only one base pair separating ureI from ureE (FIG. 1) and ureE does not have an RBS (ribosome binding site) of its own, so the expression of ureI and ureE is transcriptionally and translationally coupled. Therefore, a ureI deletion was accompanied by the addition of an RBS immediately upstream from ureE. Three intermediates, pILL824, pILL825 and pILL833 (FIG. 2A), were constructed in order to produce the final plasmid, pILL834 (FIG. 2A). A 1.8 HpaI-HindIII restriction fragment from pILL753 (9) was inserted between the EcoRV and HindIII sites of pBR322, to give pILL824. Insertion of the H19 adaptor (carrying an RBS and ATG in frame with ureE, Table 1) into a BclI site overlapping the two first codons of ureE in pILL824 produced pILL825 (FIG. 2A). The BamHI fragment of pILL825 was then replaced by a 1.3 Kb blunt-ended PvuII-BamHI fragment from pILL753. This resulted in the reconstitution of a complete ureI gene, and this plasmid was called pILL833. Finally, pILL834 was obtained by replacement of the HpaI-BglII fragment of pILL833 (thereby deleting all but the first 21 codons of ureI) with an 850 bp blunt-ended EcoRI-BamHI fragment of pUC18K2 containing the non-polar Km cassette (19).

TABLE 1

Name and nucleotide sequence oligonucleotides

| Primer | Oligodeoxynucleotide sequence (5' to 3') | |
|---|---|---|
| H17 | TTTGACTTACTGGGGATCAAGCCTG | (SEQ ID NO:1) |
| H19* | GATCATTTATTCCTCCAGATCTGGAGGAATAAAT | (SEQ ID NO:2) |
| H28 | GAAGATCTCTAGGACTTGTATTGTTATAT | (SEQ ID NO:3) |
| H34 | TATCAACGGTGGTATATCCAGTG | (SEQ ID NO:4) |
| H35 | GCAGTTATTGGTGCCCTTAAACG | (SEQ ID NO:5) |
| H50 | CCGGTGATATTCTCATTTTAGCC | (SEQ ID NO:6) |
| 8A | GCGAGTATGTAGGTTCAGTA | (SEQ ID NO:7) |
| 9B | GTGATACTTGAGCAATATCTTCAGC | (SEQ ID NO:8) |
| 12B | CAAATCCACATAATCCACGCTGAAATC | (SEQ ID NO:9) |

*H19 was used as adaptor and the others were used as primers for PCR amplification.

*H. pylori* ureI mutants were produced by allelic exchange following electroporation with a concentrated preparation of pILL823 and pILL834 as previously described by Skouloubris et al. (23) from *H. pylori* strain N6 (12) and from the mouse-adapted *H. pylori* strain, SS1 (Sydney Strain, 17). Bacteria with chromosomal allelic exchange with pILL823 were selected on Cm (4 μg/ml) and those with chromosomal allelic exchange with pILL834 on Km (20 μg/ml). It was determined that the desired allelic exchange had taken place in strains N6-823, N6-834, and SS1-834 (FIG. 1) by performing PCR with the appropriate oligonucleotides (Table 1). The PCR products obtained with genomic DNA of these strains were as expected (i) for strain N6-823: 140 bp with primers H28-H34, 220 bp with H35-9B, and 1.2 Kb with H28-9B, and (ii) for strains N6-834 and SS1-834, 150 bp with primers H28-H50, 180 bp with H17-12B, and 1 Kb with H28-12B.

The growth rate of strain N6-834 carrying a non-polar deletion of ureI was compared to that of the parental strain N6. No difference in the colony size was observed on blood agar medium plates. Identical doubling times and stationary phase OD were measured for both strains grown in BHI (Oxoid) liquid medium containing 0.2% ꓱ-cyclodextrin (Sigma). Thus, UreI is not essential for *H. pylori* growth in vitro.

Urease Activity of *H. pylori* ureI Mutants

The urease activity of strains N6-823, N6-834, and SS1-834 was measured in vitro as described previously by Cussac et al. (9) and compared to the activity of the parental strains, N6 and SS1 (FIG. 1). Urease activity was almost completely abolished in strain N6-823 (0.3±0.1 units). Strains N6-834 and SS1-834, with non-polar ureI mutations had wild-type levels of activity (N6-834 and SS1-834: 12±2 units; parental strains, N6: 10±1 and SS1: 12±0.4 units).

The pH optimum of urease produced either from the N6 parental strain or from the UreI deficient strain N6-834 was measured and compared. For both strains, urease has a pH optimum of 8 which is consistent with the published data.

These results strongly suggest that the urease-negative phenotype of the N6-ureI::TnKm-8 (13) and the very weak urease activity of N6-823 strains were due to a polar effect of the inserted cassettes on the expression of the downstream genes ureE and ureF (FIG. 1). This hypothesis was tested by measuring urease activity of strain N6-823 complemented in trans with an *E. coli/H. pylori* shuttle plasmid expressing the ureE-F genes. This plasmid, pILL845 (FIG. 2B), was obtained by insertion of a 2.8 Kb ClaI-BamHI fragment of pILL834 (comprising the 3'-end of ureB, the non-polar deletion of ureI and intact ureE and ureF genes) into the corresponding sites of the shuttle vector pHel2 constructed by Heuermann and Haas (15). Strain N6-823 was electroporated with a DNA preparation of pILL845 as described by Skouloubris et al. (23), and transformants were selected on kanamycin (20 μg/ml) and chloramphenicol (4 μg/ml). In strain N6-823 harboring pILL845, wild type urease activity was recovered confirming that the very low urease activity of strain N6-823 was due to a polar effect on the expression of the accessory genes ureE-F. In *Klebsiella aerogenes*, the absence of UreE has little effect on urease activity (4). In contrast, UreF, as part of the accessory protein complex (UreDFG), is absolutely required for the production of active urease (21). Thus, by analogy, it is likely that the phenotype of the *H. pylori* polar ureI mutants was due to the absence of ureF expression.

The urease structural subunits, UreA and UreB, produced by strain N6 or strain N6-834 were compared with the Western blot technique using a mixture of antisera directed against each urease subunit. It was observed that the amount of each subunit produced by the two strains is identical. The possibility that urease cellular localization could be affected in the absence of UreI was examined after cellular fractionation (separating the soluble from the membrane associated proteins and from the supernatant) of strains N6 and N6-834. These experiments revealed no difference between the urease cellular localization in the wild type strain or in the UreI-deficient mutant. These results demonstrate that, at neutral pH, UreI is neither implicated in the stabilization of the urease structural subunits nor in a targeting process of urease to a specific cellular compartment.

Colonization Test for the *H. pylori* SS1-834 Mutant in the Mouse Animal Model

The mouse model for infection by the *H. pylori* SS1 strain (Sydney Strain, 17), validated by Chevalier et al. (7) and Ferrero et al. (14), was used to test the function of UreI in vivo. Mice were infected with the non-polar ureI mutant, SS1-834, and with the parental strain, SS1, (which had gone through an equivalent number of in vitro subcultures) as a positive control. This experiment was repeated three times and produced identical results (30). Two independently constructed SS1-834 mutants were used. The first mutant strain had gone through 30 in vitro subcultures, the second only 20. Under the same experimental conditions, strain SS1 can undergo more than 80 in vitro subcultures without losing its colonization capacity.

In each experiment, aliquots (100 μl) containing $10^6$ H. pylori strain SS1 or SS1-834 bacteria prepared in peptone broth were administered orogastrically to 10 mice each (six to eight-weeks old Swiss specific-pathogen-free mice) as described by Ferrero et al. (14). Mice were killed four weeks after inoculation. The presence of H. pylori was tested with a direct urease test on biopsies performed on half the stomach (14). The remaining gastric tissues were used for quantitative culture of H. pylori as described by Ferrero et al. (14). In each experiment, the stomachs of the ten SS1-infected mice all tested positive for urease. The bacterial load was between $5 \times 10^4$ and $5 \times 10^5$ colony forming units (CFU) per g of stomach. None of the stomachs of the mice infected with strain SS1-834 tested positive for urease and no H. pylori cells were cultured from them. Thus, the UreI protein is essential for the H. pylori in vivo survival and/or colonization of the mouse stomach.

UreI is Essential for H. pylori Resistance to Acidity

Survival to acidic conditions in the presence or absence of 10 mM urea was tested with strains N6 and N6-834. The experimental procedures detailed in Skouloubris et al. (30) were based on those described in Clyne et al. (8). Exponentially grown bacteria were harvested, washed in PBS (phosphate buffer saline), and approximately $2 \times 10^8$ CFU/ml were resuspended in PBS of pH 2.2 or pH 7 in the presence or the absence of 10 mM urea and incubated at 37EC. After one hour incubation (i) quantitative cultures of the H. pylori strains were performed to evaluate bacterial survival, and (ii) the bacteria were centrifuged and the pH of the medium was measured. The results obtained are presented in Table 2. In the absence of urea, both strains N6 and N6-834 presented identical phenotype, i.e., they were killed at pH 2.2. and survived at pH 7 without modifying the final pH of the medium (Table 2). After incubation at pH 7 in the presence of urea, both strains were killed because the final pH rose to pH 9. At pH 2.2 in the presence of urea, the parental strain survived well since it was able to raise the pH to neutrality. In contrast, a completely different phenotype was obtained with the UreI-deficient strain N6-834 which was unable to raise the pH and whose viability was seriously affected (Table 2).

Complementation of the UreI-deficient Strain N6-834 with Plasmid pILL850

Figure 2B:
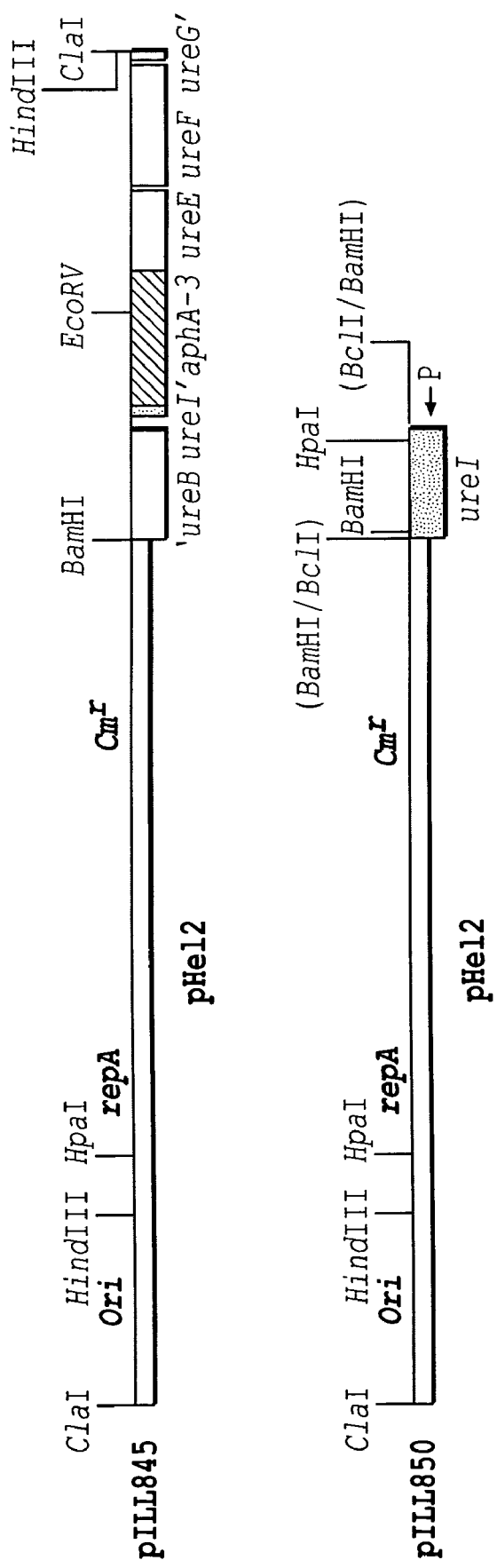
FIG. 2B depicts a restriction map of two *H. pylori/E. coli* shuttle plasmids: pILL845 and pILL850. Small boxes mark the vector of each plasmid, and large boxes correspond to genes. Ori indicates the position of the *E. coli* ColE1 origin of replication and repA the gene coding for the RepA protein necessary for autonomous replication of the pHel2 in *H. pylori*. Cm$^P$ marks the gene conferring resistance to chloramphenicol. The ureI promoter is represented by a "P" with an arrow indicating the direction of the transcription. The other symbols are as in FIG. 1.

Direct implication of the UreI protein in the H. pylori capacity to resist to acidity has been confirmed by trans-complementation with plasmid pILL850 (FIG. 2B restriction map and details of construction). This plasmid [CNCM I-2245 filed on Jun. 28, 1999] is derived from the H. pylori/E. coli shuttle vector pHel2 (15). Plasmid pILL850 carries the ureI gene under the control of its own promoter and was constructed as follows: a 1.2 kb BclI restriction fragment of plasmid pILL753 (9) was introduced between the BamHI and BclI restriction sites of pHel2 (FIG. 2B). Strains N6 and N6-834 were transformed by this plasmid and the phenotype of the complemented strains in the acidity sensitivity test experiments described above was examined. As shown in Table 2, the phenotype of strain N6-834 complemented by pILL850 is identical to that of the parental strain N6. Interestingly, the urease activity of the complemented strains (measured on sonicated extracts as described in Skouloubris et al. (30)) has been found to be significantly higher as compared to that of the corresponding strains without pILL850. For the purpose of the deposit at the CNCM pILL850 is placed into an E. coli strain, MC1061 (Wertman K F. et al, 1986, Gene 49:253-262).

Measurements Of Ammonium Production

The amount of ammonium produced in the extracellular medium of H. pylori whole cells was measured by an enzymatic assay commercialized by Sigma following the supplier's instructions. These experiments were performed after incubation of the cells in PBS at different pH values and after different incubation times. Such experiments gave an accurate evaluation of ammonium production and excretion in different strains as well as a measure of the kinetics of this reaction. A control experiment showed that ammonium production was very low (10-20 μM) in the absence of urea.

FIG. 4 depicts the kinetics (0, 3, 5, and 30 min. incubation time) of extracellular ammonium released by the N6 parental strain (panel A) and the UreI-deficient strain N6-834 (panel B) incubated in PBS at pH 2.2, pH 5, or pH 7 in the presence of 10 mM urea. The results obtained indicate that (i) ammonium is largely produced and rapidly released in the extracellular medium; and (ii) in the N6 wild type strain (FIG. 4, panel A and Table 3) ammonium production is significantly enhanced when the extracellular pH is acidic. This effect is already visible at pH 5 and is even stronger at pH 2.2. This last observation is consistent with the results of Scott et al. (31) who suggested urease activation at low pH. In our experiments, the rapidity of the response to acidity argues against urease activation depending on transcriptional regulation or on de novo protein synthesis.

Ammonium production was then measured in the UreI-deficient strain N6-834 (FIG. 4, panel B and Table 3). At neutral pH, kinetics of ammonium production were similar to those of the wild type strain. In contrast, at pH 5 ammonium production was reduced and delayed as compared to the wild type strain. A dramatic effect of the absence of UreI was observed at pH 2.2, where the amount of ammonium was very low, which is consistent with our results showing that UreI is necessary for adaptation to acidity.

Our results demonstrate that UreI is essential for the resistance of H. pylori to acidity. In the absence of UreI urease, although present in huge amounts, is not able to protect the bacteria against the aggression of acidity. This is consistent with the essential role of UreI in vivo. During its passage in the acidic stomach lumen, the viability of the UreI-deficient strain is affected. As a consequence, the bacterial load becomes too low to permit colonization. The different roles proposed for UreI are presented in the "detailed description" section.

Alignment of the UreI and AmiS Protein Sequences and Two Dimensional Structure Prediction A systematic search for UreI homologs in the protein data banks was carried out. It was determined that H. pylori is not the only ureolytic bacterium with a ureI gene. Two phylogenetically related Gram-positive organisms, Streptococcus salivarius, a dental plaque bacterium (6), and Lactobacilluis fermentum, a lactic acid bacterium (16), carry genes for UreI-homologs (FIG. 3) located immediately upstream from the urease structural genes. The ureI gene has been detected in various Helicobacter species; the H. felis ureI gene has been entirely sequenced (FIG. 3 and allowed U.S. patent application Ser. No. 08/467,822, the entire contents of which are incorporated herein by reference). PCR experiments have suggested that there is a ureI gene in *H. heilmannii* (24) and in *H. mustelae*.

Sequence similarities between the UreI protein of *H. pylori* and the AmiS proteins expressed by the aliphatic amidase operons from *P. aeruginosa* (27) and *Rhodococcus* sp. R312 (5) have been reported. In *Mycobacterium smegmatis*, there is an additional AmiS-homolog encoded by a gene, ORF P3, located immediately upstream from an amidase gene (18).

Figure 3A:
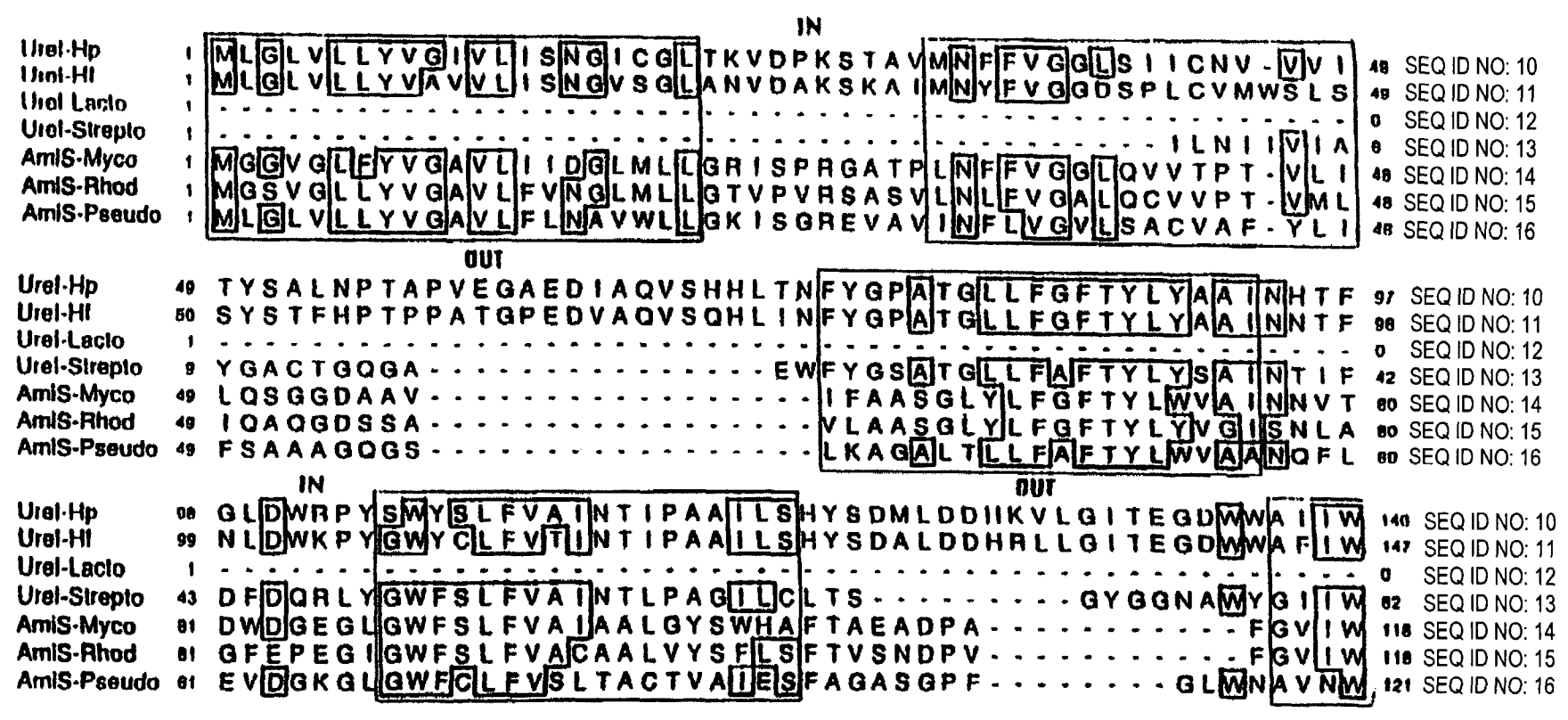
Figure 3B:
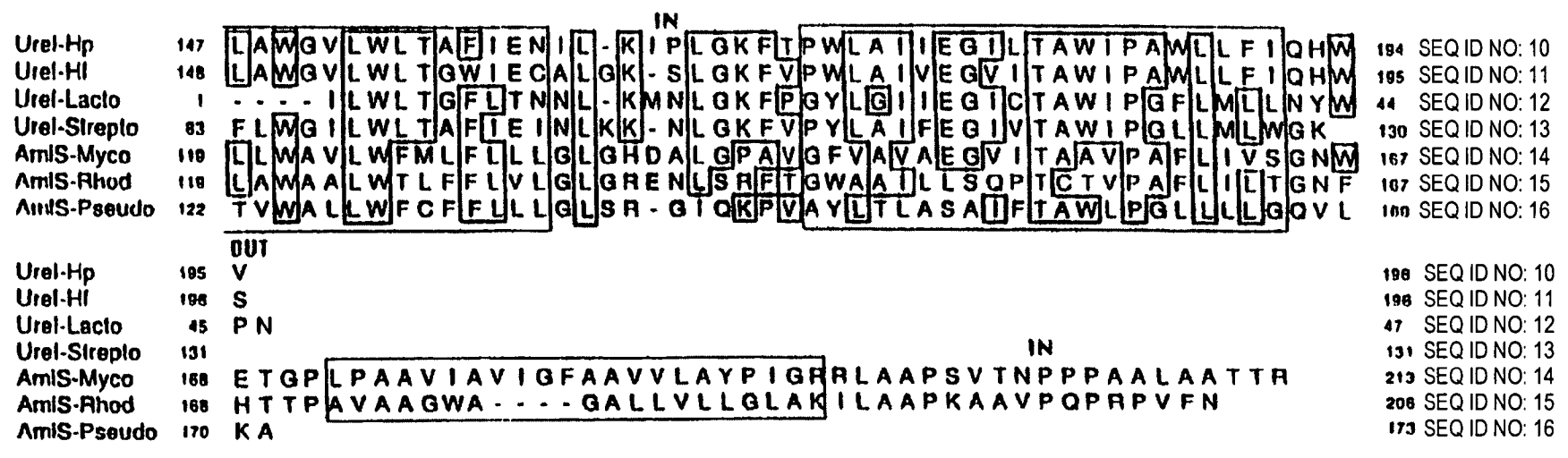

Alignment of these UreI/AmiS proteins [using the Clustal W(1. 60) program] defined strongly conserved stretches of amino acids (FIG. 3). All but one of these conserved blocks are in highly hydrophobic segments. These regions, each 17 to 22 residues long, are probably folded into transmembrane ∀-helices (FIG. 3). Six transmembrane regions were predicted for the proteins from *H. pylori*, *H. felis*, and *P. aeruginosa* and seven for those from *Rhodococcus* sp. R312 and *M. smegmatis* (highly reliable predictions, performed with pHD, a profile fed neural network system as described by Rost et al. (22)). The orientation of the UreI/AmiS proteins in the membrane was deduced from the charges of the intercalated hydrophilic regions, which are short in these proteins (FIG. 3). The first five such regions are poorly conserved and of various length. The last interhelical segment common to these proteins is significantly more conserved than the others. This region predicted to be intracellular may be the active site of UreI or a site of multimerization or interaction with an intracellular partner. These results strongly suggest that the members of the UreI/AmiS family, found in both Gram-positive and -negative bacteria, are integral membrane proteins. These proteins have no signal sequence and should therefore be inserted into the cytoplasmic membrane in Gram-negative bacteria.

Two peptides, selected from the UreI sequence, were synthesized and injected into two rabbits to obtain serum containing polyclonal antibodies directed against UreI. One peptide corresponds to the first predicted intracellular loop of UreI (from residue nB 15 to 31, see FIG. 3) and the second one to the second predicted extracellular loop of UreI (from residue nB 118 to 134, see FIG. 3. These sera are presently being tested and if proven to recognize the UreI protein will allow us to precisely define the localization of this protein and to verify the predicted UreI two-dimensional structure presented in FIG. 3.

The references cited herein are specifically incorporated by reference in their entirety.

TABLE 2

Effect of the presence of urea at pH 7, 5 or 2.2 on (i) the viability of different *H. pylori* strains and (ii) the extracellular pH (indicated as final pH). The experimental procedures are described in reference 30 and in the examples. Strain N6 is the parental strain and strain N6-834 the UreI-deficient mutant. Plasmid pILL850 is derived from a *E. coli*/*H. pylori* shuttle vector. it carries the ureI gene and complements the ureI mutation of strain N6-834.

| strains | initial pH | final pH | urea 10 mM | *H. pylori* CFU/ml |
|---|---|---|---|---|
| N6 | 2.2 | 2.26 | – | 0 |
| N6 | 2.2 | 6.6 | + | $8 \times 10^7$ |
| N6 | 7 | 6.98 | – | $2 \times 10^8$ |
| N6 | 7 | 8.88 | + | 0 |
| N6-834 | 2.2 | 2.2 | – | 0 |
| N6-834 | 2.2 | 2.37 | + | $7 \times 10^5$ |
| N6-834 | 7 | 7.1 | – | $3.5 \times 10^7$ |
| N6-834 | 7 | 9.05 | + | 0 |
| N6-834 + pILL850 | 2.2 | 2.3 | – | 0 |
| N6-834 + pILL850 | 2.2 | 6.9 | + | $1.3 \times 10^8$ |
| N6-834 + pILL850 | 7 | 7.1 | – | $1.7 \times 10^8$ |
| N6-834 + pILL850 | 7 | 9 | + | 0 |

TABLE 3

| Strain | medium pH | minutes | [NH4] mM |
|---|---|---|---|
| N6 | 7.0 | 0 | 3.5 |
| N6 | 7.0 | 3 | 4.4 |
| N6 | 7.0 | 5 | 3.1 |
| N6 | 7.0 | 30 | 5.6 |
| N6 | 5.0 | 0 | 12.8 |
| N6 | 5.0 | 3 | 9.3 |
| N6 | 5.0 | 5 | 11.8 |
| N6 | 5.0 | 30 | 16.0 |
| N6 | 2.2 | 0 | 6.7 |
| N6 | 2.2 | 3 | 9.0 |
| N6 | 2.2 | 5 | 11.0 |
| N6 | 2.2 | 30 | 20.0 |
| N6-834 | 7.0 | 0 | 2.7 |
| N6-834 | 7.0 | 3 | 2.8 |
| N6-834 | 7.0 | 5 | 3.8 |
| N6-834 | 7.0 | 30 | 5.8 |
| N6-834 | 5.0 | 0 | 1.4 |
| N6-834 | 5.0 | 3 | 1.7 |
| N6-834 | 5.0 | 5 | 2.9 |
| N6-834 | 5.0 | 30 | 4.6 |
| N6-834 | 2.2 | 0 | 0.9 |
| N6-834 | 2.2 | 3 | 0.6 |
| N6-834 | 2.2 | 5 | 0.7 |
| N6-834 | 2.2 | 30 | 1.3 |

REFERENCES

1. Akada. J. K., M. Shirai, H. Takeuchi, M. Tsuda. and T. Nakazawa. 1997. Transcriptional analysis of urease structural gene and the ureI gene in *Helicobacter pylori*. Gut. 41:A9.
2. Allaoui, A., Schulte, R. and G. R. Cornelis. 1995. Mutational analysis of the *Yersinia enterocolitica* virC operon: characterization of yscE, F, G, H, I, J, K required for Yop secretion and ysch encoding YopR. Mol. Microbiol. 18:343-355.
3. Bauerfeind, P., R. M. Garner, and H. L. T. Mobley. 1996. Allelic exchange mutagenesis of nixA in *Helicobacter pylori* results in reduced nickel transport and urease activity. Infect. Immun. 64:2877-2880.
4. Brayman, T. G., and R. T. Hausinger. 1996. Purification, characterization, and functional analysis of a truncated *Klebsiella aerogenes* UreE urease accessory protein lacking the Histidine-Rich carboxyl terminus. J. Bacteriol. 178:5410-5416.
5. Chebrou, H. F. Bigey, A. Arnaud, and P. Galzy. 1996. Amide metabolism: a putative ABC transporter in *Rhodococcus* sp. R312. Gene. 182:215-218.
6. Chen, Y.-Y. M., K. A. Clancy, and R. A. Burne. 1996. *Streptococcus salivarius* urease: genetic and biochemical characterization and expression in a dental plaque Streptococcus. Infect. Immun. 64:585-592.

7. Chevalier, C., J.-M. Thiberge, R. L. Ferrero, and A. Labigne. 1999. Essential role of *Helicobacter pylori* g-Glutamyltranspeptidase (GGT) for the colonization of the gastric mucosa in mice. Mol. Microbiol. 31:1359-1372.
8. Clyne, M., A. Labigne, and B. Drumm. 1995. *Helicobacter pylori* requires an acidic environment to survive in the presence of urea Infect. Immun. 63:1669-1673.
9. Cussac, V., R. L. Ferrero, and A. Labigne. 1992. Expression of *Helicobacter pylori* urease genes in *Escherichia coli* grown under nitrogen-limiting conditions. J. Bacteriol. 174:2466-2473.
10. Dunn. B. E., H. Cohen, and M. Blaser. 1997. *Helicobacter pylori*. Clin. Microbiol. Rev. 10:720-741.
11. Eaton, K. A., and S. Krakowka. 1994. Effect of gastric pH on urease-dependent colonization of gnotobiotic piglets by *Helicobacter pylori*. Infect. Immun. 62:3604-3607.
12. Ferrero, R. L., V. Cussac, P. Courcoux, and A. Labigne. 1992. Construction of isogenic urease-negative mutants of *Helicobacter pylori* by allelic exchange. J. Bacteriol. 174: 4212-4217.
13. Ferrero, R. L., V. Cussac, P. Courcoux, and A. Labigne. 1994. Construction of isogenic mutants of *Helicobacter pylori* deficient in urease activity. pp 179-182. In Basic and Clinical Aspects of *H. pylori* infection. Springer-Verlag Berlin Heidelberg.
14. Ferrero, R. L., J.-M. Thiberge, M. Huerre, and A. Labigne. 1998. Immune responses of specific-pathogen-free mice to chronic *Helicobacter pylori* (strain SS1) infection. Infect. Immun. 66:1349-1355.
15. Heuermann, D., and R. Haas. 1998. A stable shuttle vector system for efficient genetic complementation of *Helicobacter pylori* strains by complementation and conjugation. Mol. Gen. Genet. 257:519-528.
16. Kakimoto, S., Y. Sumino, K. Kawahara, E. Yamazaki, and I. Nakatsui. 1990. Purification and characterization of acid urease from *Lactobacillus fermentum*. Appl. Microbiol. & Biotechnol. 32:538-543;
17. Lee, A., J. O'Rourke, M. Corazon De Ungria, B. Robertson, G. Daskalopoulos, and M. F. Dixon. 1997. A standardized mouse model of *Helicobacter pylori* infection: introducing the Sydney Strain. Gastroenterology. 112:1386-1397.
18. Mahenthiralingam, E., P. Draper, E. O. Davis, and M. J. Colston. 1993. Cloning and sequencing of the gene which encodes the highly inducible acetamidase of *Mycobacterium smegmatis*. J. Gen. Microbiol. 139:575-583.
19. Menard, R., P. J. Sansonetti, and C. Parsot 1993. Nonpolar mutagenesis of the ipa genes defines IpaB, IpaC, and IpaD as effectors of *Shigella flexneri* entry into epithelial cells. J. Bacteriol. 175:5899-5906.
20. Mobley, H. L. T., M. D. Island, and R. P. Hausinger. 1995. Molecular biology of ureases. Microbiol. Rev. 59:451-480.
21. Moncrief, M. B. C., and R. P. Hausinger. 1997. Characterization of UreG, identification of a UreD-UreF-UreG complex, and evidence suggesting that a nucleotide-binding site in UreG is required for in vivo metallocenter assembly of *Klebsiella aerogenes* urease. J. Bacteriol. 179: 4081-4086.
22. Rost, B., R. Casadio, P. Fariselli, and C. Sander. 1995. Prediction of helical transmembrane segments at 95% accuracy. Prot. Science. 4:521-533.
23. Skouloubris, S., A. Labigne, and H. De Reuse. 1997. Identification and characterization of an aliphatic amidase in *Helicobacter pylori*. Mol. Microbiol. 25:989-998.
24. Solnick, J. V., J. O'Rourke, A. Lee, and L. S. Tompkins. 1994. Molecular analysis of urease genes from a newly identified uncultured species of *Helicobacter*. Infect. Immun. 62:1631-1638.
25. Trieu-Cuot, P., G. Gerbaud, T. Lambert, and P. Courvalin. 1985. In vivo transfer of genetic information between Gram-positive and Gram-negative bacteria. EMBO J. 4:3583-3587.
26. Williams, C. L., T. Preston, M. Hossack, C. Slater, and K. E. L. McColl. 1996. *Helicobacter pylori* utilizes urea for amino acid synthesis. FEMS Immunol. Med. Microbiol. 13:87-94.
27. Wilson, S. A., R. J. Williams, L. H. Pearl, and R. E. Drew. 1995. Identification of two new genes in the *Pseudomonas aeruginosa* amidase operon, encoding an ATPase (AmiB) and a putative integral membrane protein (AmiS). J. Biol. Chem. 270:18818-18824.
28. Mendz, G. L. and S. L. Mazell. 1996. The Urea Cycle of *Helicobacter pylori*. Microbiology 142:2959-2967.
29. Nicholson, E. B., E. A. Concaugh and H. L. T. Mobley. 1991. *Proteus mirabilis* urease: use of ureA-lacZ fusion demonstrates that induction is highly specific for urea. Infection and Immunity. 59(10):3360-3365.
30. Skouloubris, S., J.-M. Thiberge, A. Labigne and H. De Reuse (1998) The *Helicobacter pylori* UreI protein is not involved in urease activity but is essential for bacterial survival in vivo. Infect. Immun. 66: 4517-4521.
31. Scott, D. R., D. Weeks, C. Hong, S. Postius, K. Melchers and G. Sachs (1998) The role of internal urease in acid resistance of *Helicobacter pylori*. Gastroenterology. 114; 58-70.

We claim:

1. A method of selecting a test molecule for treating or preventing *H. pylori* infection in humans or animals comprising:
    (a) providing a UreI-positive *Helicobacter* biological sample at a neutral pH, wherein the biological sample contains UreI-positive *Helicobacter*;
    (b) providing a UreI-deficient *Helicobacter* biological sample at a neutral pH, wherein the biological sample contains UreI-deficient *Helicobacter*;
    (c) providing a UreI-positive *Helicobacter* biological sample at a second, reduced pH, wherein the biological sample contains UreI-positive *Helicobacter* in the presence of urea;
    (d) providing a UreI-deficient *Helicobacter* biological sample at a second, reduced pH, wherein the biological sample contains UreI-deficient *Helicobacter* in the presence of urea;
    (f) testing the growth or survival of the biological samples in the presence of a test molecule; and
    (g) selecting a test molecule that neither affects the growth or survival of the biological samples at a neutral pH, nor affects the growth or survival of the UreI-deficient biological sample at the second pH, but that does affect the growth or survival of the UreI-positive biological sample at the second pH.

2. The method of claim 1, wherein the test molecule affects the growth or survival of the UreI-positive *Helicobacter* biological sample at the second pH by being transported inside UreI-positive *Helicobacter* cells, but not inside UreI-deficient *Helicobacter* cells.

3. The method of claim 1, wherein the test molecule affects the growth or survival of the UreI-positive *Helicobacter* biological sample at the second pH by inhibiting resistance of UreI-positive *Helicobacter* to the second pH.

4. The method of claim 1, wherein the test molecule affects the growth or survival of the UreI-positive *Helicobacter* biological sample at the second pH by inhibiting transporter function of UreI.

5. The method of claim 1, wherein the test molecule affects the growth or survival of the UreI-positive *Helicobacter* biological sample at the second pH by inhibiting at least one interaction between UreI and at least one other *Helicobacter* protein.

6. The method of claim 1, wherein the test molecule affects the growth or survival of the UreI-positive *Helicobacter* biological sample at the second pH by inhibiting urease.

7. The method of claim 1, wherein the test molecule affects the growth or survival of the UreI-positive *Helicobacter* biological sample at the second pH by contact with UreI.

8. The method of claim 1, wherein the test molecule affects the growth or survival of the UreI-positive *Helicobacter* biological sample at the second pH by inhibiting the function of UreI in ammonia export, in urea export, or urea import.

9. The method of claim 1, wherein the UreI-positive *Helicobacter* is a UreI-deficient *Helicobacter* that has been complemented with a plasmid comprising the ureI nucleotide sequence.

* * * * *

SEQUENCE LISTING

<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
tttgacttac tggggatcaa gcctg                    25

```
<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Adaptor
      sequence

<400> SEQUENCE: 2
gatcatttat tcctccagat ctggaggaat aaat                              34

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 3
gaagatctct aggacttgta ttgttatat                                    29

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 4
tatcaacggt ggtatatcca gtg                                          23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
gcagttattg gtgcccttaa acg                                          23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 6
ccggtgatat tctcatttta gcc                                          23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
gcgagtatgt aggttcagta                                              20

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer
```

<400> SEQUENCE: 8
gtgatacttg agcaatatct tcagc                                                        25

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 9
caaatccaca taatccacgc tgaaatc                                                      27

<210> SEQ ID NO 10
<211> LENGTH: 195
<212> TYPE: PRT
<213> ORGANISM: Helicobacter pylori

<400> SEQUENCE: 10

Met Leu Gly Leu Val Leu Leu Tyr Val Gly Ile Val Leu Ile Ser Asn
 1               5                  10                  15

Gly Ile Cys Gly Leu Thr Lys Val Asp Pro Lys Ser Thr Ala Val Met
            20                  25                  30

Asn Phe Phe Val Gly Gly Leu Ser Ile Ile Cys Asn Val Val Val Ile
        35                  40                  45

Thr Tyr Ser Ala Leu Asn Pro Thr Ala Pro Val Glu Gly Ala Glu Asp
    50                  55                  60

Ile Ala Gln Val Ser His His Leu Thr Asn Phe Tyr Gly Pro Ala Thr
65                  70                  75                  80

Gly Leu Leu Phe Gly Phe Thr Tyr Leu Tyr Ala Ala Ile Asn His Thr
                85                  90                  95

Phe Gly Leu Asp Trp Arg Pro Tyr Ser Trp Tyr Ser Leu Phe Val Ala
            100                 105                 110

Ile Asn Thr Ile Pro Ala Ala Ile Leu Ser His Tyr Ser Asp Met Leu
        115                 120                 125

Asp Asp His Lys Val Leu Gly Ile Thr Glu Gly Asp Trp Trp Ala Ile
    130                 135                 140

Ile Trp Leu Ala Trp Gly Val Leu Trp Leu Thr Ala Phe Ile Glu Asn
145                 150                 155                 160

Ile Leu Lys Ile Pro Leu Gly Lys Phe Thr Pro Trp Leu Ala Ile Ile
                165                 170                 175

Glu Gly Ile Leu Thr Ala Trp Ile Pro Ala Trp Leu Leu Phe Ile Gln
            180                 185                 190

His Trp Val
        195

<210> SEQ ID NO 11
<211> LENGTH: 196
<212> TYPE: PRT
<213> ORGANISM: Helicobacter felis

<400> SEQUENCE: 11

Met Leu Gly Leu Val Leu Leu Tyr Val Ala Val Val Leu Ile Ser Asn
 1               5                  10                  15

Gly Val Ser Gly Leu Ala Asn Val Asp Ala Lys Ser Lys Ala Ile Met
            20                  25                  30

Asn Tyr Phe Val Gly Gly Asp Ser Pro Leu Cys Val Met Trp Ser Leu

```
                   35                  40                  45
Ser Ser Tyr Ser Thr Phe His Pro Thr Pro Ala Thr Gly Pro Glu
         50                  55                  60

Asp Val Ala Gln Val Ser Gln His Leu Ile Asn Phe Tyr Gly Pro Ala
 65                  70                  75                  80

Thr Gly Leu Leu Phe Gly Phe Thr Tyr Leu Tyr Ala Ala Ile Asn Asn
                 85                  90                  95

Thr Phe Asn Leu Asp Trp Lys Pro Tyr Gly Trp Tyr Cys Leu Phe Val
             100                 105                 110

Thr Ile Asn Thr Ile Pro Ala Ala Ile Leu Ser His Tyr Ser Asp Ala
         115                 120                 125

Leu Asp Asp His Arg Leu Leu Gly Ile Thr Glu Gly Asp Trp Trp Ala
130                 135                 140

Phe Ile Trp Leu Ala Trp Gly Val Leu Trp Leu Thr Gly Trp Ile Glu
145                 150                 155                 160

Cys Ala Leu Gly Lys Ser Leu Gly Lys Phe Val Pro Trp Leu Ala Ile
                165                 170                 175

Val Glu Gly Val Ile Thr Ala Trp Ile Pro Ala Trp Leu Leu Phe Ile
            180                 185                 190

Gln His Trp Ser
        195

<210> SEQ ID NO 12
<211> LENGTH: 46
<212> TYPE: PRT
<213> ORGANISM: Lactobacillus fermentum

<400> SEQUENCE: 12

Ile Leu Trp Leu Thr Gly Phe Leu Thr Asn Asn Leu Lys Met Asn Leu
 1               5                  10                  15

Gly Lys Phe Pro Gly Tyr Leu Gly Ile Ile Glu Gly Ile Cys Thr Ala
             20                  25                  30

Trp Ile Pro Gly Phe Leu Met Leu Leu Asn Tyr Trp Pro Asn
         35                  40                  45

<210> SEQ ID NO 13
<211> LENGTH: 129
<212> TYPE: PRT
<213> ORGANISM: Streptococcus salivarius

<400> SEQUENCE: 13

Ile Leu Asn Ile Ile Val Ala Tyr Gly Ala Cys Thr Gly Gln Gly
 1               5                  10                  15

Ala Glu Trp Phe Tyr Gly Ser Ala Thr Gly Leu Leu Phe Ala Phe Thr
             20                  25                  30

Tyr Leu Tyr Ser Ala Ile Asn Thr Ile Phe Asp Phe Asp Gln Arg Leu
         35                  40                  45

Tyr Gly Trp Phe Ser Leu Phe Val Ala Ile Asn Thr Leu Pro Ala Gly
     50                  55                  60

Ile Leu Cys Leu Thr Ser Gly Tyr Gly Gly Asn Ala Trp Tyr Gly Ile
 65                  70                  75                  80

Ile Trp Phe Leu Trp Gly Ile Leu Trp Leu Thr Ala Phe Ile Glu Ile
                 85                  90                  95

Asn Leu Lys Lys Asn Leu Gly Lys Phe Val Pro Tyr Leu Ala Ile Phe
             100                 105                 110

Glu Gly Ile Val Thr Ala Trp Ile Pro Gly Leu Leu Met Leu Trp Gly
```

115                 120                 125

Lys

<210> SEQ ID NO 14
<211> LENGTH: 213
<212> TYPE: PRT
<213> ORGANISM: Mycobacterium smegmatis

<400> SEQUENCE: 14

Met Gly Gly Val Gly Leu Phe Tyr Val Gly Ala Val Leu Ile Ile Asp
 1               5                  10                  15

Gly Leu Met Leu Leu Gly Arg Ile Ser Pro Arg Gly Ala Thr Pro Leu
            20                  25                  30

Asn Phe Phe Val Gly Gly Leu Gln Val Val Thr Pro Thr Val Leu Ile
        35                  40                  45

Leu Gln Ser Gly Gly Asp Ala Ala Val Ile Phe Ala Ala Ser Gly Leu
    50                  55                  60

Tyr Leu Phe Gly Phe Thr Tyr Leu Trp Val Ala Ile Asn Asn Val Thr
65                  70                  75                  80

Asp Trp Asp Gly Glu Gly Leu Gly Trp Phe Ser Leu Phe Val Ala Ile
                85                  90                  95

Ala Ala Leu Gly Tyr Ser Trp His Ala Phe Thr Ala Glu Ala Asp Pro
            100                 105                 110

Ala Phe Gly Val Ile Trp Leu Leu Trp Ala Val Leu Trp Phe Met Leu
        115                 120                 125

Phe Leu Leu Leu Gly Leu Gly His Asp Ala Leu Gly Pro Ala Val Gly
    130                 135                 140

Phe Val Ala Val Ala Glu Gly Val Ile Thr Ala Ala Val Pro Ala Phe
145                 150                 155                 160

Leu Ile Val Ser Gly Asn Trp Glu Thr Gly Pro Leu Pro Ala Ala Val
                165                 170                 175

Ile Ala Val Ile Gly Phe Ala Ala Val Val Leu Ala Tyr Pro Ile Gly
            180                 185                 190

Arg Arg Leu Ala Ala Pro Ser Val Thr Asn Pro Pro Ala Ala Leu
        195                 200                 205

Ala Ala Thr Thr Arg
    210

<210> SEQ ID NO 15
<211> LENGTH: 206
<212> TYPE: PRT
<213> ORGANISM: Rhodococcus sp.

<400> SEQUENCE: 15

Met Gly Ser Val Gly Leu Leu Tyr Val Gly Ala Val Leu Phe Val Asn
 1               5                  10                  15

Gly Leu Met Leu Leu Gly Thr Val Pro Val Arg Ser Ala Ser Val Leu
            20                  25                  30

Asn Leu Phe Val Gly Ala Leu Gln Cys Val Val Pro Thr Val Met Leu
        35                  40                  45

Ile Gln Ala Gln Gly Asp Ser Ser Ala Val Leu Ala Ala Ser Gly Leu
    50                  55                  60

Tyr Leu Phe Gly Phe Thr Tyr Leu Tyr Val Gly Ile Ser Asn Leu Ala
65                  70                  75                  80

Gly Phe Glu Pro Glu Gly Ile Gly Trp Phe Ser Leu Phe Val Ala Cys
                85                  90                  95

```
Ala Ala Leu Val Tyr Ser Phe Leu Ser Phe Thr Val Ser Asn Asp Pro
            100                 105                 110

Val Phe Gly Val Ile Trp Leu Ala Trp Ala Leu Trp Thr Leu Phe
            115                 120                 125

Phe Leu Val Leu Gly Leu Gly Arg Glu Asn Leu Ser Arg Phe Thr Gly
    130                 135                 140

Trp Ala Ala Ile Leu Leu Ser Gln Pro Thr Cys Thr Val Pro Ala Phe
145                 150                 155                 160

Leu Ile Leu Thr Gly Asn Phe His Thr Thr Pro Ala Val Ala Ala Gly
            165                 170                 175

Trp Ala Gly Ala Leu Leu Val Leu Leu Gly Leu Ala Lys Ile Leu Ala
            180                 185                 190

Ala Pro Lys Ala Ala Val Pro Gln Pro Arg Pro Val Phe Asn
            195                 200                 205

<210> SEQ ID NO 16
<211> LENGTH: 171
<212> TYPE: PRT
<213> ORGANISM: Pseudomonas aeruginosa

<400> SEQUENCE: 16

Met Leu Gly Leu Val Leu Leu Tyr Val Gly Ala Val Leu Phe Leu Asn
1               5                   10                  15

Ala Val Trp Leu Leu Gly Lys Ile Ser Gly Arg Glu Val Ala Val Ile
            20                  25                  30

Asn Phe Leu Val Gly Val Leu Ser Ala Cys Val Ala Phe Tyr Leu Ile
        35                  40                  45

Phe Ser Ala Ala Ala Gly Gln Gly Ser Leu Lys Ala Gly Ala Leu Thr
    50                  55                  60

Leu Leu Phe Ala Phe Thr Tyr Leu Trp Val Ala Ala Asn Gln Phe Leu
65                  70                  75                  80

Glu Val Asp Gly Lys Gly Leu Gly Trp Phe Cys Leu Phe Val Ser Leu
                85                  90                  95

Thr Ala Cys Thr Val Ala Ile Glu Ser Phe Ala Gly Ala Ser Gly Pro
            100                 105                 110

Phe Gly Leu Trp Asn Ala Val Asn Trp Thr Val Trp Ala Leu Leu Trp
            115                 120                 125

Phe Cys Phe Phe Leu Leu Leu Gly Leu Ser Arg Gly Ile Gln Lys Pro
    130                 135                 140

Val Ala Tyr Leu Thr Leu Ala Ser Ala Ile Phe Thr Ala Trp Leu Pro
145                 150                 155                 160

Gly Leu Leu Leu Leu Gly Gln Val Leu Lys Ala
                165                 170

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 17
tgggtgtgag atgatcata                                            19

<210> SEQ ID NO 18
<211> LENGTH: 53
<212> TYPE: DNA
```

-continued

```
<213> ORGANISM: Artificial Sequence
<220> FEATURE:
<223> OTHER INFORMATION: Description of Artificial Sequence: Adaptor
      sequence

<400> SEQUENCE: 18
tgggtgtgag atgatcattt attcctccag atctggagga ataaatgatc ata            53
```